United States Patent [19]

Miyata et al.

[11] Patent Number: 5,116,824
[45] Date of Patent: May 26, 1992

[54] BIOMATERIAL COMPRISING A COMPOSITE MATERIAL OF A CHITOSAN DERIVATIVE AND COLLAGEN DERIVATIVE

[75] Inventors: Teruo Miyata, Tokyo; Kazuhiko Kodaira, Mitaka; Hitoshi Higashijima, Koganei; Takashi Kimura, Chigasaki; Yasuharu Noishiki, Tottori, all of Japan

[73] Assignees: Katakura Chikkarin Co., Ltd.; Koken Co., Ltd., both of Tokyo, Japan

[21] Appl. No.: 603,370

[22] Filed: Oct. 29, 1990

Related U.S. Application Data

[63] Continuation of Ser. No. 854,756, Apr. 22, 1986, abandoned.

[30] Foreign Application Priority Data

May 2, 1985 [JP] Japan .................................. 60-93868

[51] Int. Cl.⁵ ...................... A61K 31/70; A01J 21/00
[52] U.S. Cl. ...................................... 514/55; 514/21; 514/54; 424/445
[58] Field of Search ...................... 514/54, 55, 56, 21; 424/78, 445

[56] References Cited

U.S. PATENT DOCUMENTS

| 4,350,629 | 9/1982 | Yannas | 260/123.7 |
| 4,407,787 | 10/1983 | Stemberger | 514/57 |
| 4,415,490 | 11/1983 | Joh | 536/128 |
| 4,559,304 | 12/1985 | Kasai et al. | 435/240 |
| 4,570,629 | 2/1986 | Widra | 128/156 |

FOREIGN PATENT DOCUMENTS

0038628 10/1981 European Pat. Off. .
0138385 4/1985 European Pat. Off. .

OTHER PUBLICATIONS

The Merck Index, 9th Ed., 1976, No. 7669, p. 1021.
Hirano, Chemical Abstracts, vol. 87 (23), p. 273, Abst. No. 180290x (1977).
Noishiki, Chemical Abstracts, vol. 95 (26), p. 376, Abst. No. 225625u (1981).

*Primary Examiner*—Johnnie R. Brown
*Assistant Examiner*—Elli Peselev
*Attorney, Agent, or Firm*—Wenderoth, Lind & Ponack

[57] ABSTRACT

A biomaterial excellent in biocompatibility comprising a composite material of an N-acylchitosan and collagen is described. This biomaterial is suitable for used as a wound dressing material, vascular prosthesis, artificial skin or hemostatic agent.

3 Claims, No Drawings

BIOMATERIAL COMPRISING A COMPOSITE MATERIAL OF A CHITOSAN DERIVATIVE AND COLLAGEN DERIVATIVE

This application is a continuation of now abandoned application Ser. No. 06/854,756 filed on Apr. 22, 1986, now abandoned.

BACKGROUND OF THE INVENTION

1. Field of the Invention

This invention relates to biomaterials excellent in biocompatibility comprising composite materials of N-acylchitosans and collagens and a process for the production thereof and more particularly, it is concerned with biomaterials which can be applied to wound dressing materials, vascular prostheses, artificial skins, hemostatic agents, etc. and a process for the production thereof.

2. Description of the Prior Art

Chitosan is a composite polysaccharide consisting of N-acetyl-D-glucosamine and D-glucosamine, obtained by deacetylation of chitin with a concentrated alkali, in which the ratio of N-acetyl-D-glucosamine and D-glucosamine varies with the degree of the deacetylation as well known in the art.

Collagen is a material that is very excellent in biocompatibility, because it is a predominant component of the connective tissue and most suitable as an extracellular matrix. Collagen has widely been used as cosmetics or biomaterials, since it has a relatively low antigenecity although in the implantation between different species, there arises a problem of antigenecity because of being a protein. A product having a very low antigenecity called atelocollagen, which product is obtained by treating tropocollagen (collagen molecule) with a proteolytic enzyme except collagenase and removing the nonhelix part (telopeptide) at the terminal of the molecule is known. This atelocollagen has significant features, i.e. the best biocompatibility of the biomaterials which have been commonly used up to the present time, because of its low antigenecity, but the range of its use is limited since when applied to a living body, collagen is absorbed by the living body in due course and is more expensive than chitosan.

A composite material of chitosan and collagen has been proposed so as to make the best use of the features of chitosan and collagen and to compensate the disadvantages thereof (U.S. Pat. No. 4,378,017). When chitosan is applied to a living body as is, however, more foreign body reactions take place as compared with collagen and a number of giant cells are found around chitosan by an optical microscope, because chitosan is a polysaccharide not present in living bodies and apparently is a foreign body to living bodies. Therefore, it is difficult to make use of chitosan alone as a biomaterial and the method of improving the biocompatibility of chitosan by adding collagen is still insufficient, so that chitosan is not put to clinical and practical use.

SUMMARY OF THE INVENTION

It is an object of the present invention to provide a biomaterial containing a chemically modified chitosan derivative, whereby the disadvantages of the prior art can be overcome.

It is another object of the present invention to provide a biomaterial which is excellent in biocompatibility.

It is a further object of the present invention to provide a chitosan derivative having an excellent biocompatibility, which can be clinically put to practical use.

It is a still further object of the present invention to provide a process for the production of the biomaterial in effective manner.

These objects can be attained by a biomaterial comprising a composite material of an N-acylchitosan and collagen or by a process for the production of a biomaterial comprising subjecting a solution of a composite material of an N-acylchitosan and collagen to freeze drying and forming a spongy product or subjecting to coating onto a base material and then drying.

DETAILED DESCRIPTION OF THE INVENTION

We, the inventors, have made various studies on chitosan and collagen for a long time and consequently, have found that a chitosan derivative obtained by chemically modifying chitosan, i.e. N-acylchitosan can sufficiently be used as a biomaterial and such a chitosan derivative can clinically be put to practical use in combination with collagen. The present invention is based on this finding.

Accordingly, the present invention provides a composite material for a medical use, comprising an N-acylchitosan and collagen. The proportion of the N-acylchitosan and collagen is preferably 1 to 99% by weight of N-acylchitosan and 99 to 1% by weight of collagen, more preferably 50 to 90% by weight of N-acylchitosan and 10 to 50% by weight of collagen.

In the composite material of the present invention, collagen means a simple substance of collagen or collagen derivatives prepared by chemically modifying collagen.

The biomaterial comprising a composite material of a N-acylchitosan and collagen according to the present invention can be prepared by subjecting the composite material in the form of a solution, dispersion or gel to freeze drying to form a spongy product, or by forming the composite material into a film or membrane.

In the composite material of the present invention, the N-acylchitosan can be a chitosan derivative obtained by modifying the amino group of chitosan with a saturated or unsaturated fatty acid of $C_1$ to $C_{32}$ and/or a dicarboxylic acid of $C_2$ to $C_8$, for example, N-acetylchitosan, N-succinylchitosan, N-hexanoylchitosan and N-myristoylchitosan.

The collagen derivative can be succinylated, acetylated or methylated collagen.

To the composite material of the present invention can preferably be added at least one member selected from the group consisting of chondroitin, chondroitin-4-sulfuric acid, dermatan sulfate, chondroitin-6-sulfuric acid, hyaluronic acid, fibronectin, fibrin, epidermal growth factors and fibroblast growth factors with a excellent wound curing effect. The thus obtained composite materials are suitable for use as artificial skins or wound dressing materials. In this case, more preferably, chondroitin, chondroitin-4 sulfuric acid, dermatan sulfate or chondroitin-6 sulfuric acid is contained in a proportion of 1 to 10% by weight, hyaluronic acid is contained in a proportion of 1 to 20% by weight, fibronectin is contained in a proportion of 0.001 to 0.01% by weight, fibrin is contained in a proportion of 0.01 to 0.1% by weight and an epidermal growth factor or fibroblast growth factor is contained in a proportion of 0.0001 to 0.001% by weight.

When heparin is contained in the composite material of an N-acylchitosan and collagen, more preferably in a proportion of 0.01 to 10% by weight, the composite material has an excellent antithrombogenicity and is suitable for use as a coating material on the wall of blood vessel or as an artificial blood vessel. When protamine is contained in the composite material of a N-acylchitosan and collagen, more preferably in a proportion of 0.1 to 20% by weight, the composite material has an excellent hemostatic effect and is suitable for use as a hemostatic agent.

In the biomaterial of the present invention, the composite material of an N-acylchitosan and collagen, which is processed in the form of a sponge or coated onto a base material, can be subjected to bridge making by treating with a bifunctional bridging agent or by irradiation. The thus bridged product can further be subjected to sterilization.

In the composite material comprising an N-acylchitosan and collagen according to the present invention, the N-acylchitosan can be prepared by acylation of chitosan. The chitosan used for the preparation of the N-acylchitosan can be any of acid-soluble ones which can be obtained by deacetylation of chitin with a concentrated alkali, but this deacetylation is preferably carried out in such a manner that the degree of deacetylation is at least 55%, more preferably 70 to 100%.

The N-acylchitosan is generally prepared by reacting such a chitosan with a carboxylic anhydride and thus effecting the N-acylation of the chitosan so as to give a chitosan acylated in a proportion of at least 55%, more preferably 70 to 100%, but the N-acylation can also be carried out after collagen is added to the chitosan. For example, N-acylchitosan is prepared by dissolving chitosan in an aqueous solution of acetic acid, diluting with methanol, mixing with carboxylic anhydride, diluting with water, subjecting to pH control with caustic soda and then subjecting to dialysis, concentration and freeze-drying in vacuum.

In the composite material of an N-acylchitosan and collagen according to the present invention, as the collagen, there can be used any of a simple substance of collagen and derivatives of collagen obtained by subjecting collagen to chemical treatments. In addition, atelocollagen with a raised biocompatibility and collagen derivatives obtained by chemically modifying collagen to raise the biocompatibility can also be used. For example, succinylated collagen obtained by treating collagen with succinic anhydride has an excellent antithrombogenicity and methylated collagen obtained by treating collagen with absolute methanol has an effect of increasing the reaction with thrombocyte. Depending upon these specific properties, therefore, various biomaterials suitable for intended uses can be obtained utilizing the chemical modification. Other reagents for the chemical modification includes, for example, absolute ethanol, 2,4-dinitrofluorobenzene, 2,4,6-trinitrobenzenesulfonic acid, hypobromites, 1,2-cyclohexanedione and the like.

The chemical modification of collagen is generally carried out by reacting collagen with a reactant or reagent, but it can of course be carried out after collagen is added to an N-acylchitosan. When the reagent for the chemical modification of collagen is a carboxylic anhydride, collagen is added to chitosan to prepare a composite material which is then reacted with the carboxylic anhydride, whereby the N-acylation of chitosan and the chemical modification of collagen can simultaneously be accomplished.

The chemical modification of collagen is predominantly carried out for the amino groups or carboxyl groups of collagen and preferably carried out in a proportion of 5 to 100%, more preferably 30 to 100% to the amino groups or carboxyl groups of collagen.

The biomaterial of the present invention can be given a water holding property by adding chondroitin, chondroitin-4 sulfuric acid, dermatan sulfate, chondroitin-6 sulfuric acid or hyaluronic acid to the composite material comprising an N-acylchitosan and collagen according to the present invention. Since these mucopolysaccharides are contained in the skin, etc. and play an important role for holding water, application of the biomaterial of the present invention, for example, to medical treatment of a wound is effective for preventing the wound surface from drying, too.

Moreover, addition of fibronectin or fibrin to the composite material of an N-acylchitosan and collagen according to the present invention results in acceleration of repairing a wound part and addition of heparin or protamine thereto results in control of the reaction with blood.

In order to improve the biocompatibility, it is required to make a biomaterial similar to the living body. The above described chemical modification and addition of the useful components occurring in the living body best answer this purpose.

The biomaterial of the present invention can be prepared by drying a composite material or composition comprising an N-acylchitosan and collagen in the form of a solution, dispersion of gel. When a solution or dispersion of the above described composite material is coated onto a surface of a base material such as glass plate and then dried, a biomaterial in the form of a film or membrane can be prepared. When the above described composite material is subjected to freeze drying, a spongy biomaterial can be prepared.

Furthermore, the strength or water absorbing capacity of the biomaterial comprising the composite material of an N-acylchitosan and collagen according to the present invention can be improved by treating the composite material with a bifunctional bridging agent or irradiating the same and thereby effecting bridge making.

As the bifunctional bridging agent in bridging of the biomaterial, any materials having two or more functional groups can be used, but hexamethylene diisocyanate or glutaraldehyde is preferably used. The bridging reaction can be carried out by adding previously a bifunctional bridging agent to a solution or dispersion of the composite material of an N-acylchitosan and collagen, forming into a film, membrane or sponge and then subjecting to bridging, or by forming the composite material of an N-acylchitosan and collagen into a film, membrane or sponge, immersing in a solution of a bridging agent or subjecting to irradiation and thereby effecting bridging. As the radiation, there can be used any of ultraviolet rays, gamma rays and corpuscular radiations such as alpha rays, but above all, ultraviolet rays or gamma rays is preferable.

The biomaterial comprising the composite material of an N-acylchitosan and collagen according to the present invention is generally used in the form of a film, membrane or sponge, but can also be used in combination with other biomaterials. The former case is exemplified by the use as a wound dressing material, artificial skin, hemostatic agent or antiadhesive membrane, and the latter case, i.e. using in combination with other biomaterials is exemplified by the use as a coating on the inside or outside of a catheter or vascular prosthesis made up of a synthetic high molecular weight material. For the use as a coating on such a biomaterial of a synthetic macromolecule, there are a method comprising immersing a biomaterial of synthetic macromolecule in a solution of the composite material of an N-acylchitosan and collagen and then drying, a method comprising applying a viscous solution or dispersion of N-acylchitosan and collagen to a biomaterial of synthetic macromolecule and then drying, and a method comprising in the above described method, carrying out drying after subjecting the coating to a chemical treatment by reacting the composite material with a carboxylic anhydride or another reactant. In such a combination of the composite material comprising an N-acylchitosan and collagen according to the present invention with another biomaterial, the surface is coated with the composite material comprising an N-acylchitosan and collagen according to the present invention and the surface of the biomaterial obtained by drying is in the form of a film or membrane, or the surface of the biomaterial obtained by freeze drying is in the form of a sponge, wherein the biocompatibility is improved.

The biomaterial comprising the composite material of a chitosan derivative and collagen according to the present invention has an excellent biocompatibility and thus can be applied to a living body in safety without any problem of antigenecity. Since the chitosan derivative is prepared from a chitosan obtained by treating chitin with a concentrated alkali in a concentration of at least 40%, in particular, the antigen-antibody reaction is remarkably reduced and the safety is increased. When the composite material of the present invention is used as a wound dressing material or artificial skin in combination with other biomaterials, healing of a wound surface is accelerated, and the composite material of the present invention having been given a thrombogenicity or antithrombogenicity can be used as a hemostatic agent or vascular prosthesis with advantageous effects.

The following examples are given in order to illustrate the present invention in detail without limiting the same.

EXAMPLE 1

Preparation of Chitosan 200 g of a crushed shell of chionoecetes was added to 2,000 ml of 5% hydrochloric acid, stirred at room temperature for 5 hours and then filtered. The residual solid product was washed with water, added to 2,000 ml of a 5% aqueous solution of sodium hydroxide, heated at 90° C. for 2.5 hours with agitation and then filtered. The residual solid product was washed with water.

The thus obtained chitin was added to 2,000 ml of a 50% aqueous solution of sodium hydroxide, heated at 90° C. for 2.5 hours with agitation and then filtered. The precipitated solid product was sufficiently washed with water and dried at 95° C., thus obtaining 41 g of chitosan with a deacetylation degree of 99%.

Preparation of Atelocollagen

A fresh calf dermis was finely crushed. 100 g of this fine powder was repeatedly washed with a 0.1M aqueous solution of sodium acetate and washed with water. To 10 g of the thus obtained fine powder was added 4,000 ml of 0.5M aqueous solution of acetic acid, followed by agitation of 5° C. for 3 days, and precipitated insoluble collagen was then separated by filtration. 10 g of the insoluble collagen was added to 100 ml of 0.1M acetic acid, to which 0.01 g of pepsin (manufactured by Sigma Co., 1:60,000) was added, and stirred at 20° C. for 3 days, thus obtaining a solution of atelocollagen (pepsin-solubilized collagen). The resulting solution of atelocollagen was filtered by a glass filter and an aqueous solution of sodium hydroxide was added to the resulting solution to adjust the pH to 7.5, thus forming a fibrous precipitate. The solution containing the precipitate was subjected to centrifugal separation at 7,000G and 8,000 rpm and the thus separated precipitate was washed with distilled water 3 times, thus obtaining 7 g of atelocollagen.

Preparation of Sponge of N-Acetylchitosan-Acetylated Collagen 18 g (0.12 mol) of the chitosan with a deacetylation degree of 99% as described above was mixed with 2 g of the atelocollagen as described above, and 20 g of this mixture was dissolved in 1,000 ml of a 2% aqueous solution of acetic acid and diluted with 2,000 ml of methanol. This solution was mixed with 24 g of acetic anhydride (corresponding to 2 molar equivalents to the hexosaminyl group of chitosan), allowed to stand at room temperature for one night and immersed in flowing water to remove the methanol and acetic acid, thus obtaining 350–380 g of a hydrated gel of a composite material of N-acetylchitosan (acetylation degree: 90%) and acetylated collagen. This gel was charged in a metallic vessel, immersed in 5,000 ml of a mixture of dry ice and methanol to freeze rapidly the gel and then subjected to freeze drying in vacuum under 0.2 mmHg to obtain 20 g of a sponge of N-acetylchitosan-acetylated collagen.

Preparation of Wound Dressing Material

The sponge of N-acetylchitosan-acetylated collagen was immersed in 10,000 ml of a 2% methanol solution of hexamethylene diisocyanate and subjected to bridging. After 2 hours, the sponge of N-acetylchitosan- and acetylated collagen was taken therefrom, washed adequately with methanol and water and then subjected to freeze drying in vacuum under 0.2 mmHg. The thus resulting sponge was sliced in a thickness of 1 mm to prepare a wound dressing material.

When this wound dressing material was applied to a wounded area on a man, a favorable healing process was found.

When the wound dressing material was applied to the back of a cavia, from which the epidermis had partly been taken off, and the healing state was observed, the sponge was fallen off to find complete healing for 10 days.

Comparative Example 1

The procedure of Example 1 was repeated except omitting the procedure of adding 24 g of acetic anhydride (corresponding to 2 molar equivalents to the hexosaminyl group of chitosan) in the preparation of a sponge of N-acetylchitosan-acetylated collagen.

When the thus resulting wound dressing material was applied to the back of a cavia, from which the epidermis had partly been taken off, and the healing state was observed, the chitosan-collagen sponge was held wet even after 10 days to show that healing was not completed.

EXAMPLE 2

Preparation of N-Succinylchitosan 2 g of the chitosan of Example 1 was dissolved in 40 ml of a 5% aqueous solution of acetic acid and diluted with 160 ml of methanol. On the other hand, 2.1 g of succinic anhydride (corresponding to 1.5 mol per 1 mol of the amino group of chitosan) was dissolved in 50 ml of acetone and the whole quantity of the resulting acetone solution of succinic anhydride was added to the above described chitosan solution, followed by allowing to stand for one night. The precipitate was separated by filtration and dried to obtain 2 g of a powder of N-succinyl-chitosan. The modification ratio of the amino groups of the chitosan amounted to 70%.

Preparation of Succinylated Collagen 2 g of collagen was dissolved in a mixed solution of 1.6 ml of concentrated hydrochloric acid and 100 ml of water, to which a 5N aqueous solution of sodium hydroxide was gradually added to adjust the pH to 13 while stirring.

On the other hand, 0.07 g of succinic anhydride (corresponding to 1 mol per 1 mol of the $\epsilon$-amino group at the side chain of collagen) was dissolved in 10 ml of acetone and the whole quantity of the acetone solution was gradually added to the above described collagen solution, followed by stirring for one night while controlling constantly the pH to 13 with a 5N aqueous solution of sodium hydroxide. The precipitate was separated by filtration, washed adequately with water and dried to obtain 2 g of succinylated collagen. The modification ration of the $\epsilon$-amino group of the collagen was 30%.

Preparation of Vascular Prosthesis 0.9 g of the thus resulting N-succinylchitosan and 0.1 g of the thus resulting succinylated collagen were dissolved in 100 ml of water, in which a vascular prosthesis (inner diameter 6 mm, length 5 cm) made of dacron whose surface had been subjected to a plasma treatment was immersed, and it was withdrawn and air-dried. After this procedure was repeated 20 times, the vascular prosthesis of dacron was immersed in a 1% aqueous solution of glutaraldehyde adjusted to pH 13 for 1 hour and thus bridged. This vaccular prosthesis of dacron was adequately washed with water and air-dried, thus obtaining a vascular prosthesis whose surface was constructed of a film of a mixture of N-succinylchitosan and succinylated collagen.

When the thus resulting vascular prosthesis was implanted in a living body, a good antithrombogenicity was obtained.

EXAMPLE 3

Preparation of Mixture of N-Succinyl-N-Octanoylchitosan and Succinylated Collagen 9 g of the N-succinylchitosan and Example 2 and 1 g of the succinylated collagen of Example 2 were dissolved in 500 ml of water and diluted with 2,000 ml of methanol, to which 22 g of octanoic anhydride (caprylic anhydride) (corresponding to 2 molar equivalents to the hexosaminyl group of chitosan) was added, and the mixture was allowed to stand at room temperature for one night to obtain a solution of a mixture of N-succinyl-N-octanoylchitosan (acylation degree: 90%) and succinylated collagen.

Preparation of Film of Biomaterial

The thus resulting solution of a mixture of N-succinyl-N-octanoylchitosan and succinylated collagen was coated onto a glass plate and then air-dried to form a film of 0.1 mm in thickness, consisting of the mixture of N-succinyl-N-octanoylchitosan and succinylated collagen, which was then bridged by irradiation of ultraviolet rays.

When this film was applied to peritoneum as an antiadhesive membrane, a good result was given that no adhesion was found.

EXAMPLE 4

Preparation of Methylated Collagen 2 g of the atelocollagen of Example 1 was immersed in 1,000 ml of a HCL-acidic solution of absolute methanol to methylate the carboxyl groups at the side chains of collagen and 2 g of a methylated collagen was obtained.

Preparation of Sponge 18 g of the chitosan of Example 1 was mixed with 2 g of the thus obtained methylated collagen and 1 g of commercially available protamine sulfate (manufactured by Wako Pure Chemical Co.) and the resulting mixture was dissolved in 1,000 ml of a 2% aqueous solution of acetic acid. This solution was diluted with 4,000 ml of methanol, mixed with 24 g of acetic anhydride (corresponding to 2 molar equivalents to the hexosaminyl group of chitosan) and allowed to stand at room temperature for one night, thus obtaining 5 kg of a mixed gel of N-acetylchitosan, methylated collagen and protamine. This gel was subjected to freeze drying in vacuum at 0.2 mmHg and a sponge of N-acetylchitosan (acetylation degree: 90%)-methylated collagen was obtained.

The resulting sponge was sliced in a thickness of 5 mm and then subjected to cross-linking and sterilization by irradiation of gamma rays of 5 megarads. When the thus obtained sponge was used as a hemostatic agent for a surgical operation, it showed an excellent effect as a hemostatic agent.

Comparative Example 2

A dog (4.5 kg, female) was subjected to an abdominal operation under general anesthesia, the edge of its spleen was excided with a depth of 5 mm, a length of 2 cm and a width of 4 mm, the hemostatic agent obtained in Example 4 was applied to the bled surface and the time until the bleeding was stopped was measured by a stopwatch to obtain 3′56″±1′21″.

For comparison, similar experiments were carried out using various known hemostatic agents, thus obtaining the following results:

| Hemostatic Agent | Time |
| --- | --- |
| (1) Helistat (commercial name made by Helitrex Inc., USA, collagen) | 4′44″ ± 0′52″ |
| (2) Spongel (commercial name made by Yamanouchi Seiyaku KK, gelatin) | 5′03″ ± 1′23″ |
| (3) Gelathrombin (commercial name made by Midori Juji KK, gelatin + thrombin) | 3′58″ ± 1′33″ |
| (4) Oxycel (commercial name made by | 4′59″ ± 0′17″ |

| -continued | |
|---|---|
| Hemostatic Agent | Time |
| Warner Lambert Co., cellulose) | |
| (5) Chitosan (deacetylation degree 99%) + Collagen, (mixing ratio 8:2) | 4'03" ± 1'19" |

EXAMPLE 5

The solution of a mixture of N-succinyl-N-octanoylchitosan and succinylated collagen obtained in Example 3 was dried in vacuum (0.1 torr) to obtain 10 g of a powder of the mixture of N-succinyl-N-octanoylchitosan and succinylated collagen. 10 g of this powder was dissolved in 50 ml of water, to which 0.1 g of chondroitin-4 sulfuric acid, 0.1 g of dermatan sulfate, 0.05 g of hyaluronic acid, 0.0001 g of fibronectin and 0.001 g of fibrin was added, and the solution was stirred by means of a homogenizer. This solution was subjected to freeze drying in vacuum at 0.2 torr. The thus obtained spongy dried product was immersed in a 2% methanol solution of hexamethylene diisocyanate, withdrawn therefrom, washed adequately with methanol, subjected again to drying in vacuum at 0.2 torr and then sliced in a thickness of 1 mm.

Fibroblasts of a rat skin was implanted in this sponge (20 mm×20 mm×1 mm), incubated at 37° C. for 2 weeks and a blast-incorporated artificial skin was obtained. When the thus obtained artificial skin was grafted on a part of the back of a rat, from which the skin had been completely lost, and a piece of the epidermis was grafted on the artificial skin, the epidermis was generated, resulting in a complete healing.

EXAMPLE 6

5 g of the gel of N-acetylchitosan and acetylated collagen obtained in Example 1 was mixed with 1 g of the methylated collagen obtained in Example 4 and 100 ml of water, adequately mixed and the pH was then adjusted to 3 by the use of 1N hydrochloric acid. 1 g of protamine was dissolved in this solution, coated onto a mesh of tetron and dried at 25° C. The coating of the solution and drying were repeated 10 times to obtain a wound dressing material consisting of the mesh of tetron and the composite material of N-acetylchitosan, acetylated collagen, methylated collagen and protamine, coated thereon in the form of films. When this wound dressing material was subjected to bridging and sterilizing by irradiation of gamma rays of 1.5 megarads and applied to a wound surface of the skin by an adhesive tape for a medical treatment, the wound part was well protected from bleeding, resulting in a good healing.

EXAMPLE 7

Preparation of Vascular Prosthesis 0.9 g of the N-succinylchitosan obtained in Example 2, 0.1 g of the succinylated collagen obtained in Example 2 and 20 mg of heparin were dissolved in 100 ml of water and a vascular prosthesis having an excellent antithrombogenicity was prepared from the resulting solution in an analogous manner to Example 2.

EXAMPLE 8

2 g of a chitosan with a deacetylation degree of 80% was dissolved in 40 ml of a 5% aqueous solution of acetic acid, mixed with 0.4 g of atelocollagen dissolved in a 5% aqueous solution of acetic acid and diluted with 160 ml of methanol. 3 g of hexanoic anhydride was dissolved in 50 ml of tetrahydrofuran, gradually added to the above described chitosan-collagen solution, adequately mixed and then cast into an aluminum vessel to give a thickness of 5 mm, followed by gelling. The resulting gel was allowed to stand for one night, washed with flowing water for 24 hours and air dried to obtain a film consisting of a composite of N-hexanoylchitosan and acylated collagen.

A mixed solution of the chitosan and collagen was prepared in an analogous manner, to which a solution of 3 g of myristic anhydride in 50 ml of tetrahydrofuran was then added, and from the resulting solution was similarly obtained a film consisting of a composite of N-myristoylchitosan and acylated collagen.

On the other hand, the same mixed solution of the chitosan and collagen was cast into an aluminum vessel to give a thickness of 5 mm and air dried to obtain a film consisting of the chitosan and collagen for comparison.

When the thus obtained three films were cut in a size of 1 cm×3 cm, inserted in a subcutaneous tissue on the back of a grown dog, taken out after 6 weeks, and the tissue piece was observed by an optical microscope to estimate the biocompatibility, giant cells were caused by foreign bodies and collected repeatedly to show a remarkable foreign body reaction in the case of the film consisting of the composite of the chitosan and collagen, while a few giant cells caused by foreign bodies collected around but a foreign body reaction was nonsignificant in the cases of the films consisting of the composite of the N-hexanoylchitosan and acylated collagen, and the composite of the N-myristoylchitosan and acylated collagen.

It is apparent from these results that the films consisting of the composites of N-acylchitosans and acylated collagens meet with less foreign matter reactions and have a more excellent biocompatibility.

What is claimed is:

1. A wound dressing material comprising a composite material of an N-succinylchitosan and atelocollagen in a proportion of 50 to 90% by weight of the N-succinylchitosan to 10 to 50% by weight of the compound selected from the group consisting of atelocollagen, acetylated atelocollagen and methylated atelocollagen, the composite material being crosslinked and in the form of a sponge or film and the N-succinylchitosan being obtained by succinylation of chitosan prepared by deacetylation of chitin with a concentrated alkali to form a chitosan succinylated in a proportion of at least 55%.

2. The wound dressing material according to claim 1 wherein the atelocollagen is acetylated or methylated.

3. The wound dressing material of claim 1, wherein the composite material further contains at least one member selected from the group consisting of chondroitin-4 sulfuric acid, dermatan sulfate, chondroitin-6 sulfuric acid, hyaluronic acid, and fibrin.

* * * * *